US012790462B2

(12) United States Patent
Linghu et al.

(10) Patent No.: US 12,790,462 B2
(45) Date of Patent: Nov. 10, 2026

(54) VOLATILE OR SEMI-VOLATILE NATURAL ANTIOXIDANTS SOURCED FROM A COMESTIBLE BYPRODUCT

(71) Applicant: Kellanova, Battle Creek, MI (US)

(72) Inventors: Ziyi Linghu, Battle Creek, MI (US); John David Pinkston, Battle Creek, MI (US)

(73) Assignee: KELLANOVA, Battle Creek, MI (US)

( * ) Notice: Subject to any disclaimer, the term of this patent is extended or adjusted under 35 U.S.C. 154(b) by 95 days.

(21) Appl. No.: 18/661,868

(22) Filed: May 13, 2024

(65) Prior Publication Data

US 2024/0301167 A1 Sep. 12, 2024

Related U.S. Application Data

(62) Division of application No. 17/252,011, filed as application No. PCT/US2019/037944 on Jun. 19, 2019, now Pat. No. 12,006,416.

(Continued)

(51) Int. Cl.

| | |
|---|---|
| ***C09K 15/08*** | (2006.01) |
| ***A23B 2/733*** | (2025.01) |
| ***A23B 2/746*** | (2025.01) |
| ***A23B 9/26*** | (2006.01) |
| ***A23L 3/3472*** | (2006.01) |
| ***A23L 5/20*** | (2016.01) |
| ***B65D 65/40*** | (2006.01) |

(Continued)

(52) U.S. Cl.

CPC ................ *C08K 5/13* (2013.01); *A23B 2/733* (2025.01); *A23B 2/746* (2025.01); *A23B 9/26* (2013.01); *A23L 5/21* (2016.08); *B65D 65/40* (2013.01); *B65D 81/28* (2013.01); *C07C 41/09* (2013.01); *C07C 41/40* (2013.01); *C07C 43/23* (2013.01); *C09K 15/08* (2013.01); *A23L 5/15* (2016.08); *A23L 5/17* (2016.08); *A23V 2002/00* (2013.01); *A23V 2200/02* (2013.01)

(58) Field of Classification Search

None

See application file for complete search history.

(56) References Cited

U.S. PATENT DOCUMENTS 5,002,989 A * 3/1991 Naumovitz .............. C08K 3/32 524/109
5,169,660 A 12/1992 Collins et al.

(Continued)

FOREIGN PATENT DOCUMENTS

CN 101402657 A 4/2009
EP 1369407 A1 12/2003

(Continued)

OTHER PUBLICATIONS

PCT/US2019/037944 International Search Report dated Sep. 10, 2019.

(Continued)

*Primary Examiner* — Richard A. Huhn
(74) *Attorney, Agent, or Firm* — Honigman LLP

(57) ABSTRACT

A method of obtaining a volatile or semi-volatile natural antioxidant by toasting a comestible byproduct, natural antioxidants obtained by toasting the comestible byproduct, and packaging films incorporating such natural antioxidants are described herein.

7 Claims, 7 Drawing Sheets

Related U.S. Application Data

(60) Provisional application No. 62/687,576, filed on Jun. 20, 2018.

(51) Int. Cl.

| | |
|---|---|
| ***B65D 81/28*** | (2006.01) |
| ***C07C 41/09*** | (2006.01) |
| ***C07C 41/40*** | (2006.01) |
| ***C07C 43/23*** | (2006.01) |
| ***C08K 5/13*** | (2006.01) |
| *A23L 5/10* | (2016.01) |

(56) References Cited

U.S. PATENT DOCUMENTS

| | | | |
|---|---|---|---|
| 6,572,915 B1 | 6/2003 | Van Drunen et al. | |
| 2010/0112181 A1 | 5/2010 | Taylor et al. | |
| 2010/0240769 A1 | 9/2010 | Tornberg et al. | |
| 2018/0290811 A1* | 10/2018 | Withers | B32B 27/306 |

FOREIGN PATENT DOCUMENTS

| | | | |
|---|---|---|---|
| GB | 2506667 | A | 4/2014 |
| WO | 9114738 | A1 | 10/1991 |
| WO | 2013171545 | A1 | 11/2013 |
| WO | 2017049364 | A1 | 3/2017 |

OTHER PUBLICATIONS

Busolo, et al., Antioxidant polyethylene films based on a resveratrol containing clay of intrest in food packaging applications, Food Packaging and Shyelf Life, vol. 6, Sep. 2, 2015, pp. 30-41.

Guillen, et al., New Components with Potential Antioxidant and Organoleptic Properties, Detected for the First Time in Liquid Smoke Flavoring Preparations, J. Agric. Food Chem, vol. 46, 1998, pp. 1276-1285.

Park, Hye-Yeon, et al., Development of Antioxidant Packaging Material by Applying Corn-Zein to LLDPE Film in Combination with Phenlic Compounds, J of Dood Science, vol. 77, No. 10, Aug. 31, 2012, pp. 273-279.

Santos-Sanchez, Norma F. et al., Natural antioxidant extracts as food preervatives, Acta Sci. Pol. Technil. Aliment, vol. 16, No. 4, Oct. 1, 2017, pp. 361-370.

Somnuk et al.: "Optimization of coffe oil extraction from spent coffe grounds using four solvents and prototype-scale extraction using circulation process", Department of Mechanical Engineering, Faculty of Engineering, Prince of Songkla University, Hat Yai, Sonkhla, 90112, Thailand, Agriculture and Natural Resources 51 (2017), pp. 181-189.

* cited by examiner

VOLATILE OR SEMI-VOLATILE NATURAL ANTIOXIDANTS SOURCED FROM A COMESTIBLE BYPRODUCT

CROSS-REFERENCE TO RELATED APPLICATIONS

This application is a divisional application of U.S. patent application Ser. No. 17/252,011, filed Dec. 14, 2020, which is a National Stage Application and claims priority under 35 U.S.C. § 371 to Patent Cooperation Treaty application PCT/US2019/037944, filed Jun. 19, 2019, which claims the benefit of and priority under 35 U.S.C. § 119(e) to U.S. Provisional Application No. 62/687,576, filed Jun. 20, 2018. Priority is claimed to these applications and the disclosures of these prior applications are considered part of the disclosure of this application, and to the extent allowed, the entire contents of the aforementioned applications are incorporated herein.

FIELD

The present disclosure relates generally to a method of obtaining volatile or semi-volatile natural antioxidants from comestible byproducts and, in particular, toasted comestible byproducts, to the natural antioxidants obtained therefrom, and to packaging films incorporating such natural antioxidants.

BACKGROUND

Butylated hydroxytoluene (BHT) is a synthetically produced compound commonly used as an antioxidant and preservative. BHT is often incorporated into food packaging by impregnating the BHT into plastic liners or film used to make the food packaging. In use, the BHT migrates out of the packaging over time to interact with the food and helps prevent spoilage of the food. Other synthetically produced antioxidants, such as tert-butylhydroquinone (TBHQ) or butylated hydroxyanisole (BHA) are sometimes used in place of BHT in a similar manner.

TBHQ, BHA, and BHT are synthetic chemicals and becoming less desired by consumers. Consumers have shown a growing preference for more natural preservatives, rather than synthetically produced compounds. However, using natural preservatives and antioxidants in place of BHT, BHA, and TBHQ present challenges. Attempts have been made, for example, to use mixed tocopherols and/or rosemary extract in place of the BHT, BHA, or TBHQ. However, these options are more expensive and do not function as an antioxidant as well as BHT, BHA, or TBHQ. Mixed tocopherols and rosemary extract are also not volatile or even semi-volatile and, thus, need to be applied directly to foods rather than impregnated in packaging in order to function as antioxidants. Because these alternative antioxidants need to be applied directly to the foods, they may degrade due to the application method and/or subsequent processing of the food (such as cooking under pressure, heating, drying, etc.) Rosemary extract may also impart unwanted flavors and/or aromas to the foods it is attempting to protect. Thus, current natural alternatives to BHT, BHA, and TBHQ exhibit several shortcomings.

SUMMARY

In one aspect, a method of obtaining a volatile or semi-volatile natural antioxidant from a comestible byproduct is provided. In some embodiments or approaches, the methods include providing a comestible byproduct having a source of phenolic compounds and optionally grinding the comestible byproduct. The method further incudes toasting the comestible byproduct or optionally ground comestible byproduct for a time and at a temperature effective to volatilize and thermally convert the phenolic compounds of the comestible byproduct or the optionally ground comestible byproduct into volatilized compounds including one or more substituted phenolic compounds, and recovering the volatilized compounds including the one or more substituted phenolic compounds for use as the volatile or semi-volatile natural antioxidant.

In other aspects, the method of the previous paragraph may be combined with one or more optional features individually or in any combinations thereof. These optional features include one or more of the following: wherein the comestible byproduct is selected from canola meal, wheat bran, pomace, straw, coffee fruit, green coffee bean, roasted coffee beans, roast and ground coffee, spent coffee grounds, and combinations thereof; and/or wherein the toasting includes dry heating at atmospheric pressure for about 10 minutes to about 20 minutes at about 165° C. to about 250° C., optionally under an inert gas purge; and/or wherein the recovering includes cold trapping of the volatilized compounds; and/or further comprising incorporating the recovered volatilized compounding including the one or more substituted phenolic compounds into a polymer substrate for use as packaging material; and/or wherein the polymer substrate is selected form polyethylene, low density polyethylene (LDPE), linear low density polyethylene (LLDPE), ethylene-vinyl acetate (EVA), polypropylene, polylactic acid (PLA), metalocene, polybutylene, and mixtures thereof; and/or wherein the one or more substituted phenolic compounds include one or more substituted methoxy phenol compounds; and/or wherein the one or more substituted phenolic compounds include a 4,6-subustituted 2-methoxy phenol or derivative thereof; and/or wherein the 4,6-substitution is selected from hydrogen, a methoxy group, a methyl group, a vinyl group, and combinations thereof; and/or wherein the volatile or semi-volatile antioxidant has a vapor pressure from about 0.0005 mm to about 0.5 mm of Hg at about 25° C.

In yet further aspects, a packaging film including a volatile or semi-volatile natural antioxidant sourced from a toasted comestible byproduct is provided. The packaging film may include a flexible packaging film having an amount of a natural antioxidant sourced from a toasted comestible byproduct. In one approach, the natural antioxidant may be any of the antioxidants as described in the previous two paragraphs. In other approaches, the natural antioxidant may include a 4,6-substituted 2-methoxy phenol or derivative thereof.

In yet further aspects, the packaging film of the previous paragraph may be combined with one or more optional features either individually or in any combination. These optional features include one or more of the following: wherein the 4,6-substitution is selected from hydrogen, a methoxy group, a methyl group, a vinyl group, and combinations thereof; and/or wherein the natural antioxidant is selected from 2-methoxy-4-methylphenol, 2-methoxyphenol, 2,6-dimethoxyl-4-vinylphenol, substituted vinyl phenols, derivatives thereof, and combinations thereof; and/or wherein the natural antioxidant is obtained from toasting a phenolic-acid and/or polyphenolic containing comestible byproduct; and/or wherein the polyphenolic and/or phenolic-acid containing comestible byproduct is selected from canola meal, wheat bran, pomace, straw, coffee, coffee beans, coffee fruit, roast and ground coffee, spent coffee grounds, and combinations thereof; and/or wherein the toasting includes dry heating at atmospheric pressure for about 10 minutes to about 20 minutes at about 165° C. to about 250° C., optionally under an inert gas purge; and/or wherein the flexible packaging film includes polyethylene, low density polyethylene (LDPE), linear low density polyethylene (LLDPE), ethylene-vinyl acetate (EVA), polypropylene, polylactic acid (PLA), metalocene, polybutylene, and mixtures thereof; and/or wherein the flexible packaging film is a multi-layer film and wherein one of the layers includes the amount of the natural antioxidant; and/or wherein another of the layers in the multi-layer film is a barrier layer selected from high density polyethylene (HDPE), polyvinylidene chloride (PVDC), ethylene-vinyl alcohol copolymer (EVOH), and combinations thereof; and/or wherein the amount of the natural antioxidant in the packaging film limits the amount of hexanal formation from a food source prone to oxidation to less than about 3 ppm after 12 weeks of storage at about 90° F. to about 101° F.

In another aspect, a volatile or semi-volatile natural antioxidant obtained from a toasted comestible byproduct is provided herein. The volatile or semi-volatile natural antioxidant may include a compound of Formula I:

(Formula I)

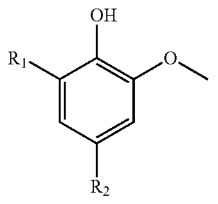

wherein $R_1$ and $R_2$ are independently selected from a hydrogen, an alkoxy group, an alkyl group having C1 to C6 carbon atoms, and a C1 to C6 hydrocarbyl group including one or more vinyl carbons therein (in other approaches, a C1 to C4 carbon group or C2 to C4 hydrocarbyl group). Any of the previously described aspects may also include the natural antioxidant of Formula I as described in this paragraph or the following paragraph.

The volatile or semi-volatile natural antioxidant of the previous paragraph may also be combined with one or more optional features either individually or in any combination thereof. These optional features include one or more of the following: wherein the volatile or semi-volatile natural antioxidant has a vapor pressure of about 0.0005 mm Hg at 25° C. to about 0.5 mm Hg at 25° C.; wherein $R_1$ is hydrogen and $R_2$ is a methyl group; wherein $R_1$ is a methoxy group and $R_2$ is a C2 vinyl group; wherein $R_1$ is hydrogen and $R_2$ is a C2 vinyl group; and/or wherein the compound of Formula I is derived from a toasted phenolic-acid or polyphenolic containing comestible byproduct; and/or wherein the phenolic-acid or polyphenolic containing comestible byproduct is selected from canola meal, wheat bran, pomace, straw, coffee, coffee beans, coffee fruit, roast and ground coffee, spent coffee grounds, and combinations thereof.

DRAWINGS

The drawings described herein are for illustrative purposes only of selected configurations and not all possible implementations, and are not intended to limit the scope of the present disclosure;

DETAILED DESCRIPTION

Figure 1:
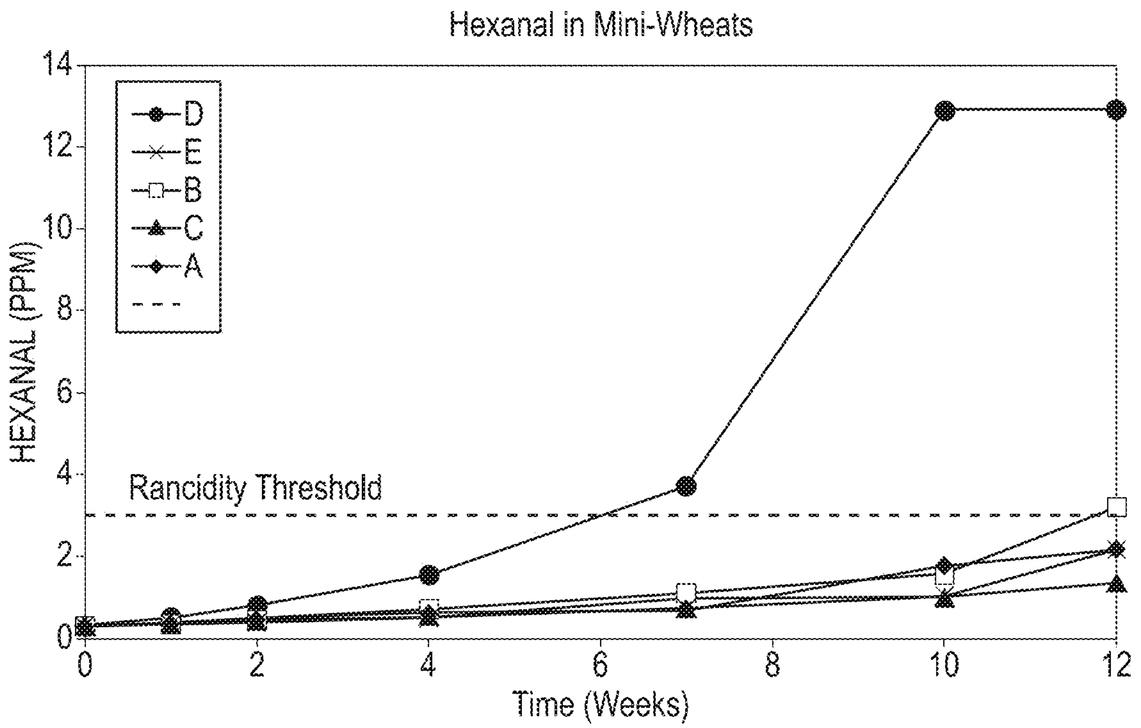
FIG. 1 is a chart of hexanal concentration over time during a shelf life study using antioxidants available from comestible sources.

Disclosed herein are methods of obtaining volatile or semi-volatile natural antioxidants from comestible byproducts, the resulting natural antioxidants obtained from the comestible byproducts, and packaging films incorporating such natural antioxidants. In one aspect, the methods described herein provide the volatile or semi-volatile natural antioxidant from a comestible byproduct that includes a source of polyphenolic and/or phenolic acid compounds. The selected comestible byproduct may be heated or toasted to volatilize and convert the polyphenolic and/or phenolic acid compounds of the comestible byproduct into the volatile or semi-volatile natural antioxidants. It is believed that the selected comestible byproducts themselves, however, do not include the compounds providing the antioxidant functionality (or include only small or negligible amounts), but the methods herein include processing conditions and recovery methods to obtain the desired volatile and/or semi-select volatile compounds and convert target compounds therein into those with antioxidant functionality in a quantity sufficient to provide the desired antioxidant effect.

In some aspects, the recovered natural antioxidants herein include one or more substituted phenolic compounds, such as substituted methoxy phenol compounds, and the like, that are volatilized and thermally converted from polyphenolic and/or phenolic acid compounds in the starting comestible byproduct. The methods herein also provide for recovering the volatilized and converted compounds for use as the natural antioxidants. In some approaches, the recovery methods include natural recovery methods devoid of organic solvents and the like so that even after recovery, the antioxidants remain natural.

It was discovered that certain comestible byproduct streams including sources of select polyphenolic and/or phenolic acid compounds could be processed to volatilize and convert the select compounds therein into a material with antioxidant activity similar to and/or better than BHT, BHA, and TBHQ. As discussed herein, and with any embodiment of this disclosure, the methods recover natural antioxidants from the starting comestible byproduct by converting, transforming, and volatilizing the compounds. The converting and volatilizing may occur simultaneously or in any order. That is, the converting and volatilizing may occur at the same time, or the compound may first be converted and volatilized, or vice versa or any combination thereof depending on the starting material and particular compound. It was discovered that by dry heating or toasting the comestible byproduct for an effective time and temperature, certain compounds therein could be volatilized and converted into the new substituted phenolic compound, such as methoxy phenol compounds, that have high antioxidant activity. The volatilized compounds could then be isolated for use as preservatives/antioxidants and used with foods and/or incorporated into food packaging films (e.g., plastic liners) similar to BHT, BHA and TBHQ. A shelf-life study of the naturally-sourced and naturally-produced volatile antioxidants showed that they are effective for preventing rancidity of cereal similar to or better than BHT.

The antioxidants described herein are produced naturally by dry heating or toasting the comestible byproduct, thereby producing volatilized and converted compounds, and thereafter capturing the volatilized compounds (in some cases, using natural capturing methods). The comestible byproduct(s) are selected due to a source of polyphenolic and/or phenolic acid compounds that can easily be converted into the desired antioxidants that are volatilized by the dry heating or toasting process. In some approaches, the comestible byproducts can optionally be ground in order to increase surface area for the heating/toasting process and release of volatilized compounds. The dry heating or toasting process is performed for a time and temperature effective to volatize and thermally convert the polyphenolic and/or phenolic acid compounds of the comestible byproduct into volatilized compounds including, in some approaches, one or more substituted methoxy phenol compounds. The volatilized compounds are recovered for use as antioxidants, which can be incorporated into packaging, such as a food liner.

Turning to more of the specifics, the starting comestible byproduct is a processed comestible or other spent food product that preferably includes a source of polyphenolic and/or phenolic acid compounds. The natural antioxidants herein are derived from sources that would otherwise have little or no practical use and commonly discarded. For example, the comestible byproduct may be selected from (to suggest but a few sources of polyphenolic and/or phenolic acid compounds) canola meal, bran (wheat bran, corn bran, and the like and mixtures thereof) pomace (e.g., olive, grape, and the like and mixtures thereof), straw, green coffee bean, roasted coffee beans, roast and ground coffee, spent coffee grounds, coffee fruit, soybean residue (residue after the oil and protein removal) and combinations thereof. The comestible byproducts can be obtained from wheat milling companies, olive producers, the wine industry, or the canola oil industry to suggest a few sources. The select byproduct(s) are a source of polyphenolic and/or phenolic acid compounds, which, when dry heated or toasted as described herein release volatilized compounds that are also converted into one or more substituted phenol compounds (such as substituted methoxy phenolic compounds as further discussed herein) that are effective as natural antioxidants as discussed further herein. Optionally, the starting comestible byproduct may be ground prior to the heating to increase surface area. Grinding may be through any suitable method to obtain a particle size of about 1 mm to about 3 mm in size using conventional grinding equipment. In some approaches, the concentration of phenolic and polyphenolic compounds in the starting comestible byproduct may be about 20 mg/g GAE to about 2,200 mg/g GAE (gallic acid equivalent), but such levels may vary depending on the starting material source.

The volatilized and converted compounds recovered from the byproduct include one or more volatile or semi-volatile antioxidants and have antioxidant functionality. The volatile or semi-volatile antioxidants derived and converted from the comestible byproducts include at least one or more substituted phenol compounds, such as one or more methoxy phenol compounds, which are believed to contribute significantly to the antioxidant properties of the recovered volatilized compounds.

In some approaches, the one or more methoxy phenol compounds may include 4,6-substituted 2-methoxy phenol or derivatives thereof. The 4,6 substitution may be selected from hydrogen, methoxy, methyl, vinyl and combinations thereof. The one or more methoxy phenol compounds may include, but not limited to, for example, 2-methoxy-4-methylphenol, 2,6-dimethoxy-4-vinylphenol, 2-methoxy-4-vinylphenol, and mixtures thereof. The volatile or semi-volatile antioxidants may also include other volatile or semi-volatile antioxidants in addition to the methoxy phenol compounds herein. The volatile or semi-volatile antioxidants may advantageously have little or no aroma as compared to other natural antioxidants with strong characteristic aroma (such as the prior rosemary extracts, for example). Advantageously, the volatile or semi-volatile natural antioxidants herein have a volatility consistent to BHT, BHA, and TBHQ and, in some approaches, may have a vapor pressure of about 0.0005 mm to about 0.5 mm of Hg at 25° C.

In other approaches or embodiments, the volatile or semi-volatile natural antioxidants obtained from the methods herein and from a dry heated or toasted comestible byproduct include at least a compound of Formula I:

(Formula I)

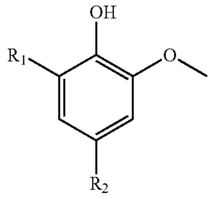

wherein $R_1$ and $R_2$ are independently selected from a hydrogen, an alkoxy group, an alkyl group having $C_1$ to $C_6$ carbon atoms, and a $C_1$ to $C_6$ hydrocarbyl group including one or more vinyl carbons therein. In some embodiments, $R_1$ is hydrogen and $R_2$ is a methyl group. In other embodiments, $R_1$ is a methoxy group and $R_2$ is a C2 vinyl group. And in other embodiments, $R_1$ is hydrogen and $R_2$ is a C2 vinyl group.

The toasting process of the select comestible byproducts herein may include dry heating or toasting the comestible byproduct at atmospheric pressure for about 10 to about 20 minutes at about 165° C. to about 250° C., optionally under an inert gas purge. (In other approaches, for a time ranging from at least about 10 minutes, at least about 12 mins, at least about 14 min, or at least about 16 min to less than about 20 mins, less than about 18 mins, less than about 16 mins, or less than about 14 mins. In other approaches, a temperature ranging from at least about 165° C., at least about 170° C., at least about 180° C., at least about 190° C., or at least about 200°° C. to less than about 250° C., less than about 240° C., less than about 230° C., less than 220° C., or less than about 210° C.) During the dry heating or toasting, it is believed that the comestible byproducts or portions thereof may undergo pyrolysis that thermally degrades non-volatile lignins present in the byproduct materials; thus, producing a range of semi-volatile and volatile substances including those described above.

Figure 3:
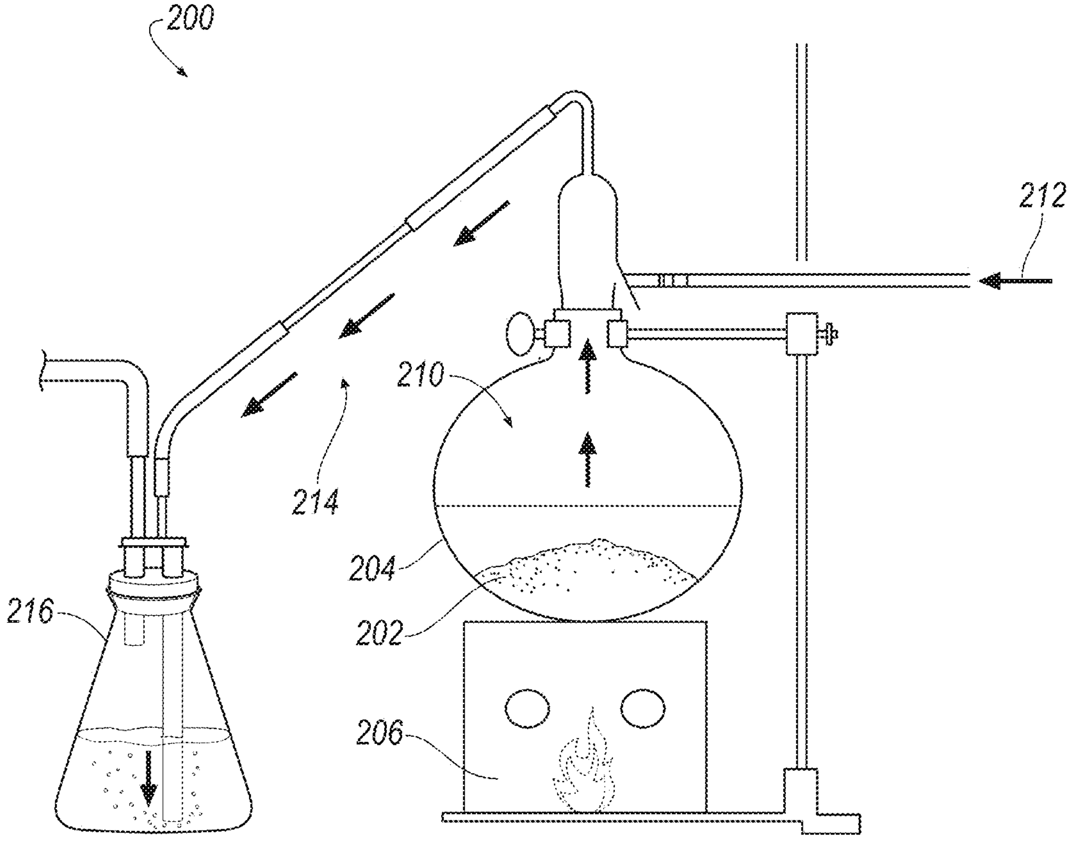
FIG. 3 is a schematic of a bench scale process for producing and capturing natural antioxidants from a comestible.
Figure 4:
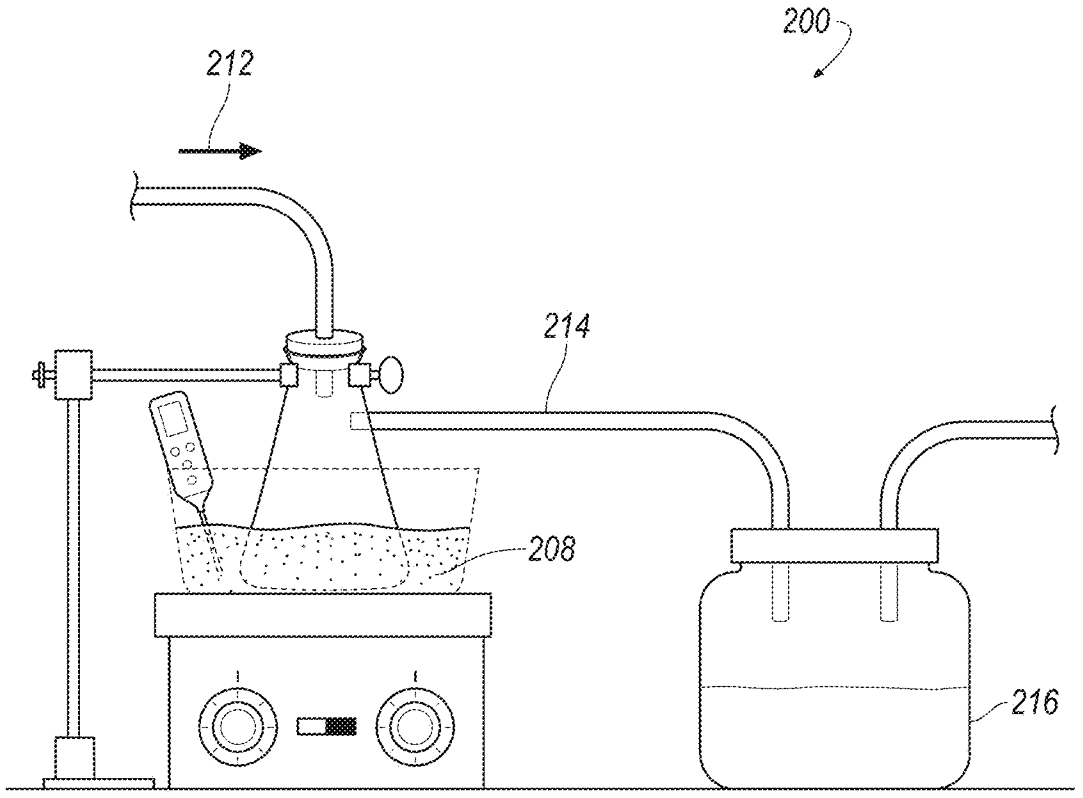
FIG. 4 is an example of a bench scale set-up for producing and capturing natural antioxidants from a comestible.
Figure 5:
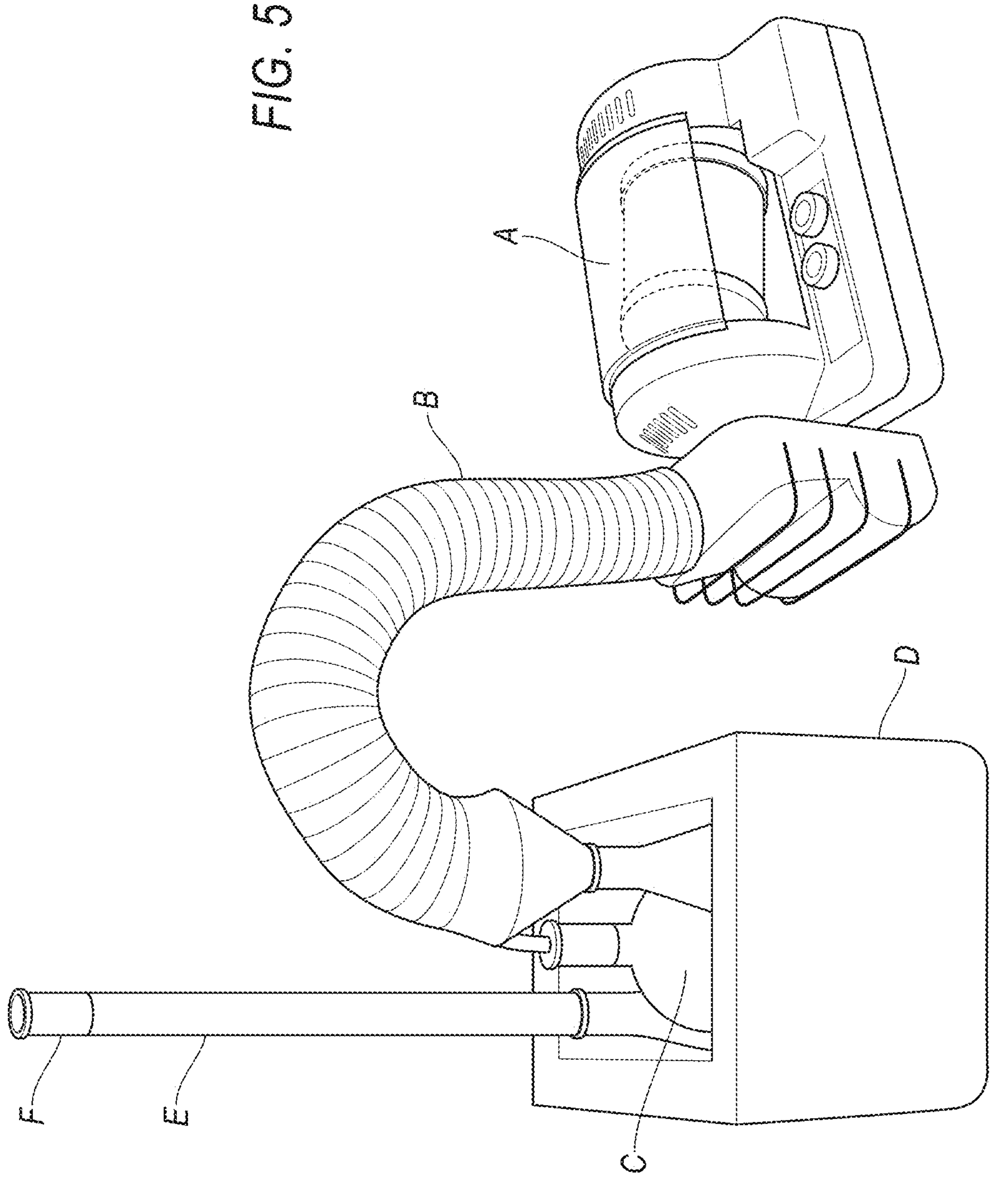
FIGS. 5 and 6 are images of an exemplary cold trapping system.
Figure 6:
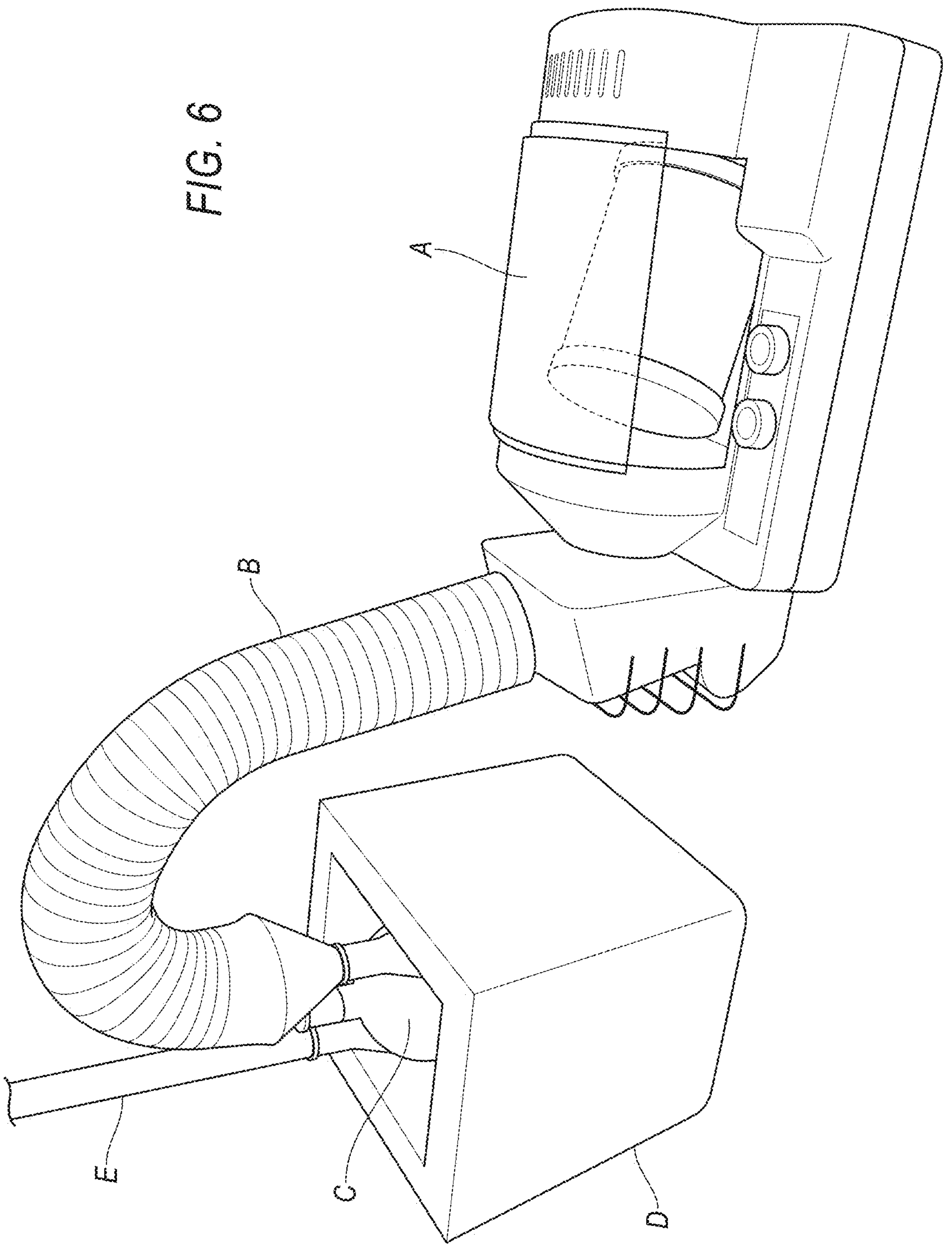

Recovery of the volatilized and converted compounds released from the dry heating or toasting the byproducts can be performed using natural recovery methods. For example, FIGS. 3 and 4 show a schematic and experimental set-up for isolating the volatilized compounds released from toasting a comestible byproduct. The process in FIGS. 3 and 4 is described in Example 3 and involves purging the released volatilized compounds with inert gas and trapping in a solvent bath. Alternatively, non-solvent methods may be employed such as cold trapping of the volatilized compounds. FIGS. 5 and 6 illustrate an exemplary cold trapping system showing a roaster A (controls roasting temperature and time, provides a gentle flow of air to sweep volatiles and semi-volatiles toward the cold trap, rotates food byproduct as it is roasting to distribute heat), a transfer line B from the roaster A to a cold trap C (a round bottom flask sitting in an ice bath D), a Vigreux column E (traps more semi-volatiles from exhaust), and an exhaust E of gases into a fume hood. Cold trapping may include a flask connected to the outlet of the roaster, and immersed in an ice bath. The volatiles and semi-volatiles produced during roasting move into the flask and are trapped on the cold walls of the flask. An air-cooled Vigreux column may be placed at the exit of the flask, which helps cold trap more of the volatilized molecules. Advantageously, the volatilized and converted compounds are easily separated and isolated from their source as compared to non-volatile compounds that may require extensive solvent extraction and purification steps to achieve desired purity.

The volatile or semi-volatile antioxidants herein may be added to, incorporated with, impregnated, or blended into a polymer substrate for use as a packaging material similar to BHT, BHA, or TBHQ. This can be done in accordance with the known methods for incorporating semi-volatile antioxidants, such as BHT, into polymers and other films commonly used as a packaging material, where the natural volatile or semi-volatile antioxidants herein are configured to migrate out of the polymer, film, or other packaging material and onto the food stored with the packaging material over time similar to BHT. The natural antioxidants described herein are advantageously volatile or semi-volatile to a similar level as BHT, which allows them to be incorporated into the polymer or packaging material and then migrate out of the packaging material and onto food during storage to prevent oxidative rancidity development. In some approaches, about 600 ppm to about 2000 ppm of the natural antioxidant herein (in other approaches, amounts ranging from at least about 700 ppm, at least about 900 ppm, at least about 900 ppm, at least about 1000 ppm, or at least about 1200 ppm to less than about 2000 ppm, less than about 1800 ppm, less than about 1600 ppm, or less than about 1400 ppm) may be provided in conventional packaging films and function to limit the amount of hexanal formation from a food source prone to oxidation to less than about 3 ppm (such about 0.5 to less than about 3ppm, about 1 to about 2.5, or about 1 to about 2 ppm hexanal) after 12 weeks of storage at about 70° F. to about 95° F. (in other approaches, about 70° F. to about 85° F.).

A packaging film may be provided including the volatile or semi-volatile antioxidants sourced from a toasted comestible byproduct as described herein. The packaging film may be a flexible packaging film. The antioxidants may include 4,6-substituted 2-methoxy phenols or derivatives thereof, or any antioxidant as described herein. In some embodiments, the packaging film or packaging material comprises a polymer substrate selected from polyethylene, low density polyethylene (LDPE), linear low density polyethylene (LLDPE), ethylene-vinyl acetate (EVA), polypropylene, polylactic acid (PLA), metalocene, polybutylene, and mixtures thereof.

In some embodiments, the flexible packaging film is a multi-layer film wherein one of the layers includes the amount of the antioxidants as described herein. Another of the layers in the multi-layer film may be a barrier layer selected from high density polyethylene (HDPE), polyvinylidene chloride (PVDC), ethylene-vinyl alcohol copolymer (EVOH), and combinations thereof. The packaging film may be a breathable or non-breathable film. The volatile or semi-volatile antioxidants described herein can be incorporated into a plastic liner, coated on the packaging, or laminated into a pouch. Alternatively, the natural antioxidants herein may be applied directly to a food.

The practice and advantages of the disclosed embodiments may be demonstrated by the following Examples, which are presented for purposes of illustration and not limitation. Unless indicated otherwise, all amounts, percentages, parts, and ratios of this disclosure and below Examples are by weight.

EXAMPLES

Example 1

This Example describes screening experiments for natural and semi-volatile antioxidants. Three compounds were screened for their ability to prevent rancidity in a shelf-life study. The three compounds evaluated for antioxidant functionality included Sample A (2-methoxy-4-methylphenol, Sigma-Aldrich), Sample B (2,6-dimethoxy-4-vinylphenol, Sigma-Aldrich), and Sample C (2-methoxy-4-vinylphenol, Sigma-Aldrich).

Kellogg's unfrosted Mini-Wheats® cereal (shredded wheat cereal) was used in a shelf-life study comparing the preservative ability of the three compounds against a control with no added antioxidant (Sample D) and against a control with added BHT (Sample E, Sigma-Aldrich). For the evaluation, about 10 mg of each compound was placed inside a high barrier bag with the cereal at about 100° F. and about 35 percent relative humidity. The antioxidant sample was weighed and the appropriate amount added to the bag and then sealed.

Hexanal content is a marker to measuring rancidity of foods and about 3 ppm of released hexanal from a food is a threshold of perceived rancidity for most consumers. Hexanal content is measured by the following procedures: A cereal sample is removed at the appropriate shelf-life time point. About 0.5 grams of the cereal sample is mixed with about 5.0 mL of deionized water and sealed. About 0.5mL of headspace from the sealed sampled cereal is removed and the hexanal response is determined by GC with FID detection. The concentration of hexanal is determined based on a calibration curve made using hexanal standards in water. In part, the method is based upon: Hexanal as a Measure of Rancidity in Low Fat Foods, C. W. Fritsch, J. A. Gale, JAOCS, Volume 54, June 1977, p. 226-228 providing a list of the sources of information relating to the assay's development (ADAC, AACC, etc.), which is incorporated herein by reference.

FIG. 1 and Table 1 below provide the hexanal content (ppm) in the cereal over the course of 12 weeks during the shelf-life study. After seven weeks, the control sample D with no added antioxidant had a hexanal content above the 3 ppm threshold and would be perceived as rancid by most consumers. The three experimental antioxidants samples A, B, and C and the BHT control sample E each hindered hexanal content to a similar manner and prevented hexanal content from rising above the perceived rancidity level over the course of the 12-week study period (with the exception of the final time point with sample B at 12 weeks that had a hexanal level of 3.21 ppm). The hexanal-in-food concentrations for the 12-week shelf-life study are presented in Table 1 below and shown in FIG. 1.

TABLE 1

| Hexanal content (ppm) vs Age (weeks) | | | | | | | | |
|---|---|---|---|---|---|---|---|---|
| Sample | | Shelf-life Age, 100° F., 35% RH (Weeks) | | | | | | |
| ID | | 0 | 1 | 2 | 4 | 7 | 10 | 12 |
| D | Control | 0.32 | 0.52 | 0.83 | 1.56 | 3.74 | 12.90 | 12.92 |
| E | Control | 0.29 | 0.33 | 0.38 | 0.49 | 0.98 | 1.04 | 2.16 |
| B | Inventive | 0.30 | 0.38 | 0.49 | 0.71 | 1.10 | 1.57 | 3.21 |
| C | Inventive | 0.28 | 0.35 | 0.41 | 0.54 | 0.75 | 1.01 | 1.36 |
| A | Inventive | 0.30 | 0.35 | 0.47 | 0.62 | 0.69 | 1.77 | 2.17 |

As can be seen in Table 1, compounds A and C had a similar or better ability to mitigate the development of rancidity than the BHT control sample E. Compound B mitigated rancidity development in comparison to control sample D, but had a slightly weaker ability to mitigate rancidity compared to the BHT control Sample E.

Example 2

Based on the screening study of Example 1, various food byproducts that could potentially provide the source of the selected compounds of Example 1 were identified. The food byproducts were then toasted, and the antioxidant activity of the toasted food byproducts was evaluated.

For this Example, canola meal (ADM), red wheat bran (Knappen Milling Company, Augusta, MI) and olive pomace (Il Fiorello Olive Oil Co., Fairfield, CA) were tested as sources of compounds capable of providing the compounds screened in Example 1. For example, it is believed that olive pomace upon toasting will produce 2-methoxy-4-methyl phenol; canola meal upon toasting will produce 2, 6-dimethoxy-4-vinyl phenol; and red wheat bran upon toasting will produce 2-methoxy-4-vinyl phenol. About 5 grams of each food byproduct was toasted at 230° C. for 20 minutes.

Figure 2:
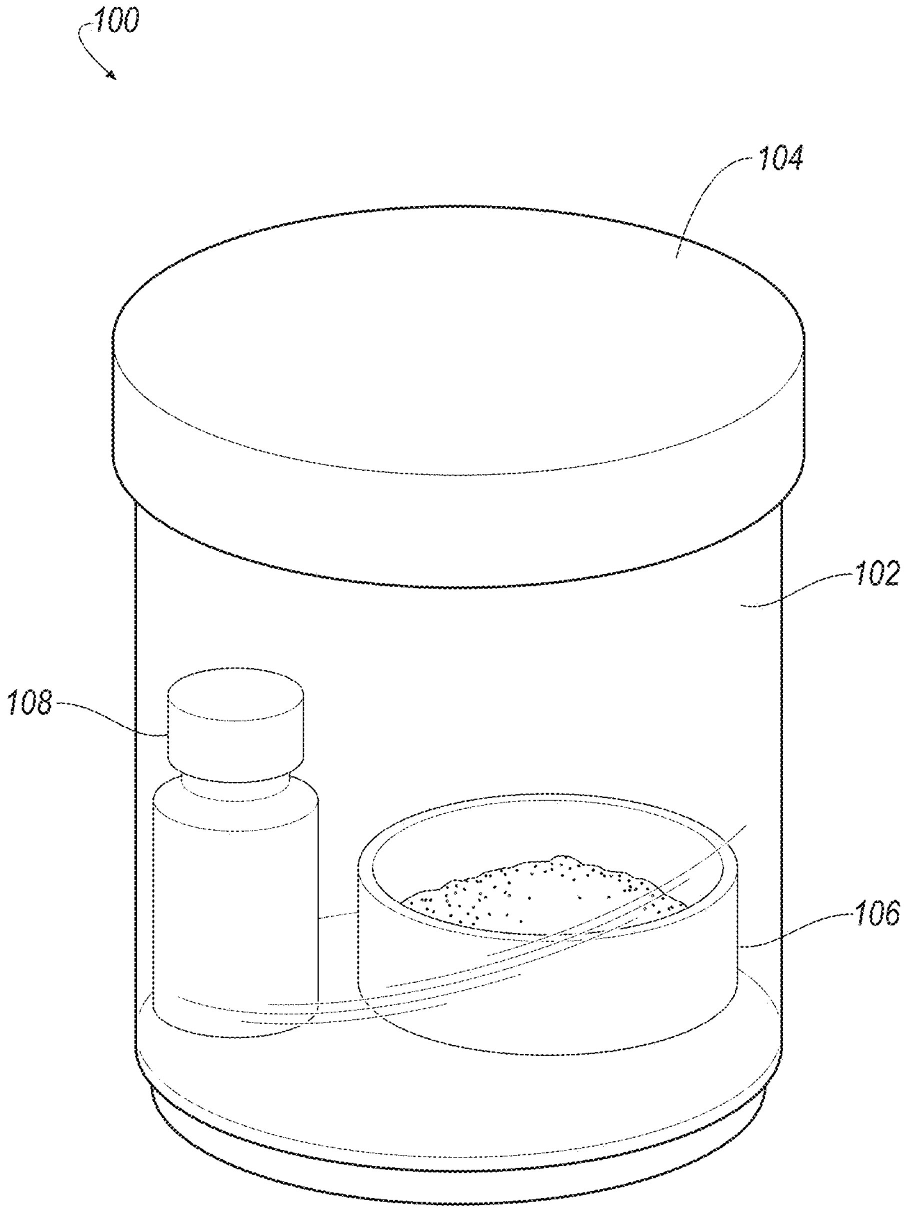
FIG. 2 is a diagram and chart showing toasting of comestible byproducts and testing of the toasted comestible byproducts in a DPPH (2.2-diphenyl-1-picrylhydrazyl) free-radical scavenging test cell.

To evaluate the semi-volatile antioxidant functionality, the residue from the 5 gram toasted byproduct material (slightly less than 5 grams in mass) was placed inside a volatile—or semi-volatile-antioxidant test cell 100 as shown in FIG. 2. The cell 100 consisted of a wide mouth glass jar 102 with a plastic screw-top lid 104 and an approximate volume of 200mL. As shown in FIG. 2, the toasted byproduct (slightly less than 5 grams) was placed in a small Petri dish 106 inside the cell, and a vial 108 containing 2mL of 0.1 mM of DPPH (2.2-diphenyl-1-picrylhydrazyl) in methanol solution, open to the atmosphere inside the cell, was placed next to the Petri dish. The cell 100 was placed in the dark at room temperature (about 70° F. to about 75° F.) for about 17 hours. Only volatile and semi-volatile materials that move from the toasted byproduct into the DPPH solution can exhibit DPPH free radical scavenging activity. As an indication of antioxidant activity, the percent of DPPH free radical scavenging activity of the volatile and semi-volatile materials in the toasted byproduct was measured using the procedure as described in Brand-Williams, W., et al. (1995), "Use of a free radical method to evaluate antioxidant activity," LWT-Food Science and Technology 28(1): 25-30; O. P. Sharma and T. K. Bhat, "DPPH Antioxidant Assay Revisited," Food Chemistry 113 (2009) 1202-1205; and P. Jing et al., "Quantitative Studies on Structure—DPPH Scavenging Activity Relationships of Food Phenolic Acids," Molecules 17 (2012), 12910-12924, which are all incorporated herein by reference. DPPH free radical scavenging is a measure of antioxidant activity.

FIG. 2 shows a diagram of the toasting and testing cell. The results of the percent DPPH assay are also presented in Table 2. Percent DPPH free radical scavenging is calculated as follows: The absorbance of the DPPH free radical is measured with a UV/VIS spectrophotometer at 515 nm. No antioxidant (a blank) provides a large absorbance at 515 nm, which is defined as 0% free-radical scavenging. A strong antioxidant would eliminate all absorbance at 515 nm; thus, no absorbance at 515 nm provides 100% free-radical scavenging. The volatile and semi-volatile components of the toasted byproducts reduce the absorbance by varying amounts under the test conditions, which provide various %-free-radical-scavenging values. The smaller the absorbance at 515 nm, the higher the % free-radical-scavenging antioxidant activity. Ten milligrams of pure BHT is used as a positive control. An empty Petri dish is used as the negative control. The results were compared to a BHT control.

TABLE 2

| Sample ID | Material | % DPPH free radical scavenging |
|---|---|---|
| F | Toasted Canola meal | 93% |
| G | Toasted Red wheat bran | 47% |
| H | Toasted Olive pomace | 18% |
| I | BHT (control) | 57% |

Example 3

In this Example, a system was developed for capturing the antioxidants from the toasted food byproduct. A schematic of the system 200 is shown in FIG. 3 and a schematic of an alternative embodiment of the system 200 is shown in FIG. 4. The food byproduct 202 is placed in an Erlenmeyer or round-bottom flask 204. The flask is heated, e.g., with a flame or with a hot plate or other heat source 206. The flask may be in a sand bath, with the hot plate heating the sand bath, for uniform heat transfer. The applied heat source dry heats or toasts the food byproduct, which volatilizes the desired compounds from the food byproduct and also converts nonvolatile materials into the desired volatile or semi-volatile compounds, which are volatilized. The volatilized compounds are released into the head space 210 of the flask. A purging gas 212, such as nitrogen or other inert gas, is flowed 214 into the head space and out of the flask into a collecting flask or jar 216. In one approach, the collecting flask contains a solvent and also has a head space. The volatilized compounds flow into the solvent in the collecting flask and are trapped in the solvent. The remaining purging gas rises from the trapping solvent into the headspace of the collecting flask and is vented out of the collecting flask. The trapping solvent is removed by gentle evaporation under a stream of dry nitrogen. The evaporative process cools the solvent and minimizes losses of the semi-volatile antioxidants. Once most of the solvent is removed, the remaining solution is moved to a glass vial, and the evaporation process continues until all the solvent is removed. Aliquots of the residue are massed and used directly, or a small volume of solvent is added back to allow aliquoting and quantitative comparisons of the semi-volatile antioxidants contained in the residue.

In an alternate example, cold trapping may include a flask connected to the outlet of the roaster, and immersed in an ice bath as shown in FIGS. 5 and 6 and its accompanying discussion above. The volatiles and semi-volatiles produced during roasting move into the flask and are trapped on the cold walls of the flask. An air-cooled Vigreux column E is placed at the exit of the flask, which helps cold trap more of the volatilized molecules.

Example 4

This Example provide a longer shelf life study with antioxidants as described herein obtained from toasted food byproducts per the methods of Examples 1 to 3.

Volatilized and thermally converted compounds produced and captured according to the process in Examples 2 and 3 were extracted and tested in a shelf-life study. For this study, the samples of Table 3 below were evaluated for the prevention or control of hexanal generated from Unfrosted Mini-Wheats® cereal (shredded wheat cereal) over a period of 14 weeks. No BHT or any other antioxidant were added to the shredded wheat cereal during production, transportation, or storage until this experiment began.

TABLE 3

| Test Samples | | |
|---|---|---|
| Sample | Source | Amount |
| J | Control-No antioxidant | N/A |
| K | Control-BHT (Sigma-Aldrich) | 300 μg |
| L | 2-methoxy-4-vinylphenol (Sigma-Aldrich) | 300 μg |
| M | 2-methoxy-4-methylphenol (Sigma-Aldrich) | 300 μg |
| N | Toasted wheat bran per procedures of Example 3 | 5 g |
| O | Toasted olive pomace per procedures of Example 3 | 5 g |
| P | Toasted canola meal per procedures of Example 3 | 5 g |
| Q | Toasted olive pomace volatile and semi-volatile extract | 600 μg |
| U | Toasted canola meal volatile and semi-volatile extract | 600 μg |
| R | Toasted red wheat bran volatile and semi-volatile extract | 600 μg |

For the evaluation, separate film pouches made from polyethylene film (film was permeable to the test samples) were filled with each of the test samples of Table 3 and then sealed. The procedure for samples K, L, and M: about 100 μL of an about 3000 ppm solution of each in methanol was placed in the pouch. The methanol was then evaporated under a gentle stream of dry nitrogen leaving about 300 μg of the dry pure compound in the pouch. The procedure for samples Q, U, and R: about 100 μL of an about 6000 ppm solution of each in methanol was placed in the pouch. The methanol was then evaporated under a gentle stream of dry nitrogen leaving about 600 μg of the extract in the pouch.

Figure 7:
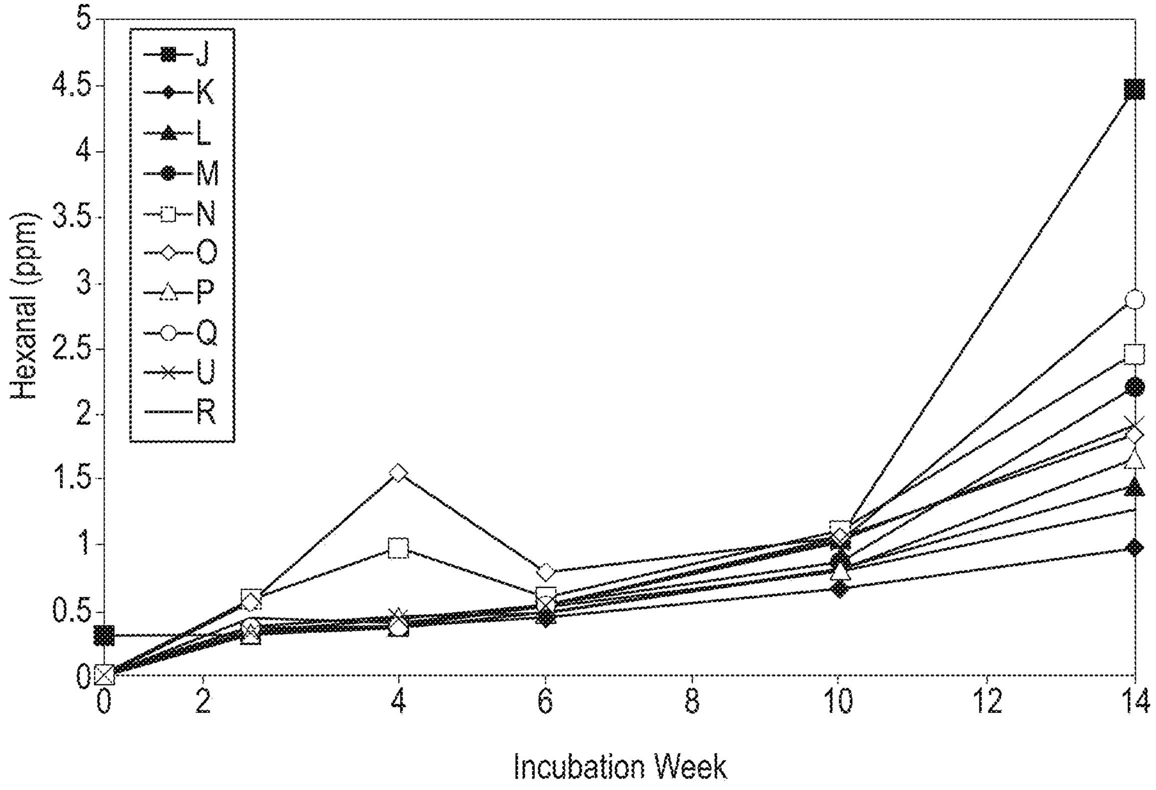
FIG. 7 is a chart of hexanal concentration over time during a shelf-life study using antioxidants described herein.

The pouch was then inserted into a package fabricated from high-barrier metalized film (high barrier metalized film prevents ingress or egress of oxygen, volatile, and semi-volatile organic molecules) along with about 20 grams of Unfrosted Mini-Wheats® cereal and the pouch and cereal were then sealed in the package. An empty film pouch was used as control sample J. The pouches were co-packed with the cereal and stored at about 100° F. for about 14 weeks. Every two weeks the hexanal content of the co-packed material was evaluated by hexanal-in-food analysis as described in Example 1. The hexanal content (ppm) over 14 weeks for each sample is shown in Table 4 below and FIG. 7. The volatile extracts were effective in moving through the pouch material and acting as antioxidant preservatives, preventing oxidative rancidity of the cereal, as shown by comparison to BHT and the other comparative samples.

TABLE 4

| | | Hexanal ppm | | | | | |
|---|---|---|---|---|---|---|---|
| ID | Sample | T0 | T2 | T4 | T6 | T10 | T14 |
| J | Control | 0.301 | 0.316 | 0.380 | 0.537 | 1.05 | 4.47 |
| K | BHT - Control | N/A | 0.33 | 0.363 | 0.439 | 0.656 | 0.968 |
| L | 2-methoxy-4-vinylphenol | N/A | 0.309 | 0.364 | 0.468 | 0.815 | 1.44 |
| M | 2-methoxy-4-methylphenol | N/A | 0.335 | 0.391 | 0.537 | 0.861 | 2.20 |
| N | Toasted Wheat Bran | N/A | 0.576 | 0.972 | 0.589 | 1.10 | 2.45 |
| O | Toasted Olive Pomace | N/A | 0.56 | 1.54 | 0.785 | 1.05 | 1.84 |
| P | Toasted Canola Meal | N/A | 0.376 | 0.444 | 0.482 | 0.798 | 1.65 |
| Q | Olive Pomace Volatile Extract | N/A | 0.355 | 0.383 | 0.531 | 1.02 | 2.87 |
| U | Canola Meal Volatile Extract | N/A | 0.325 | 0.430 | 0.527 | 1.02 | 1.90 |
| R | Red Wheat Volatile Extract | N/A | 0.436 | 0.381 | 0.522 | 0.781 | 1.26 |

Example configurations are provided above so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed. If a range is described herein, it will be appreciated that any endpoint within the range may be included within this discussion.

The foregoing description has been provided for purposes of illustration and description. It is not intended to be exhaustive or to limit the disclosure. Individual elements or features of a particular configuration are generally not limited to that particular configuration, but, where applicable, are interchangeable and can be used in a selected configuration, even if not specifically shown or described. The same may also be varied in many ways. Such variations are not to be regarded as a departure from the disclosure, and all such modifications are intended to be included within the scope of the disclosure.

What is claimed is:

1. A packaging film including a natural antioxidant sourced from a toasted comestible byproduct, the packaging film comprising:

a flexible packaging film having an amount of a natural antioxidant sourced from a toasted comestible byproduct; and the natural antioxidant is a residue obtained from toasting a phenolic-acid and/or polyphenolic containing comestible byproduct and including a compound of Formula I:

(Formula I)

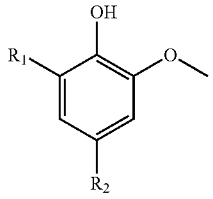

derived from a toasted comestible byproduct of canola meal, wheat bran, pomace, straw, coffee fruit, green coffee bean, roasted coffee beans, roast and ground coffee, spent coffee grounds, and combinations thereof, wherein R1 and R2 are independently selected from a hydrogen, an alkoxy group, an alkyl group having C1 to C6 carbon atoms, and a C2 to C6 hydrocarbyl group including one or more vinyl carbons therein.

2. The packaging film of claim 1, wherein the natural antioxidant comprises 2-methoxy-4-methylphenol, 2-methoxyphenol, 2,6-dimethoxy-4-vinylphenol, substituted vinyl phenols, derivatives thereof, and combinations thereof.

3. The packaging film of claim 1, wherein the toasting includes dry heating at atmospheric pressure for about 10 minutes to about 20 minutes at about 165° C. to about 250° C., optionally under an inert gas purge.

4. The packaging film of claim 1, wherein the flexible packaging film includes polyethylene, low density polyethylene (LDPE), linear low density polyethylene (LLDPE), ethylene-vinyl acetate (EVA), polypropylene, polylactic acid (PLA), polybutylene, and mixtures thereof.

5. The packaging film of claim 1, wherein the flexible packaging film is a multi-layer film and wherein one of the layers includes the amount of the natural antioxidant.

6. The packaging film of claim 5, wherein another of the layers in the multi-layer film is a barrier layer selected from high density polyethylene (HDPE), polyvinylidene chloride (PVDC), ethylene-vinyl alcohol copolymer (EVOH), and combinations thereof.

7. The packaging film of claim 1, wherein the amount of the natural antioxidant in the packaging film limits the amount of hexanal formation from a food source prone to oxidation to less than about 3 ppm after 12 weeks of storage at about 90 to about 101° F.

* * * * *